(12) United States Patent  (10) Patent No.: US 7,338,417 B2
Kang  (45) Date of Patent: Mar. 4, 2008

(54) PERINEUM MUSCULAR POWER INCREASE DEVICE AND A METHOD THEREOF

(76) Inventor: Byung Mo Kang, 12/3, 387-104, Shipjeong-2dong, Bupycong-gu, 403-132 Incheon (KR)

( * ) Notice: Subject to any disclaimer, the term of this patent is extended or adjusted under 35 U.S.C. 154(b) by 189 days.

(21) Appl. No.: 10/534,967
(22) PCT Filed: Nov. 4, 2003
(86) PCT No.: PCT/KR03/02336

§ 371 (c)(1),
(2), (4) Date: May 16, 2005

(87) PCT Pub. No.: WO2004/045411

PCT Pub. Date: Jun. 3, 2004

(65) Prior Publication Data

US 2006/0047225 A1  Mar. 2, 2006

(30) Foreign Application Priority Data

Nov. 18, 2002  (KR) .................. 10-2002-0071745
Nov. 30, 2002  (KR) .................. 10-2002-0076437
Oct. 30, 2003  (KR) .................. 10-2003-0076500

(51) Int. Cl.
    A63B 23/00  (2006.01)
(52) U.S. Cl. ................... 482/148; 600/591
(58) Field of Classification Search ........... 482/148; 600/591, 549, 29, 38, 41, 373, 375; 128/898, 128/778; 607/138, 116
See application file for complete search history.

(56) References Cited

U.S. PATENT DOCUMENTS

| 4,216,783 | A | | 8/1980 | Kaiser et al. ............ 600/591 |
| 5,531,226 | A | | 7/1996 | Harris .................... 600/587 |
| 5,904,660 | A | * | 5/1999 | Kim ..................... 601/108 |
| 6,059,740 | A | | 5/2000 | Leivseth et al. .......... 600/591 |
| 6,223,750 | B1 | * | 5/2001 | Ishikawa et al. .......... 128/885 |
| 6,432,037 | B1 | | 8/2002 | Eini et al. ............... 600/29 |
| 2003/0195094 | A1 | * | 10/2003 | Kim ..................... 482/142 |
| 2004/0005972 | A1 | * | 1/2004 | Sugiyama et al. ......... 482/148 |

* cited by examiner

Primary Examiner—Lori Amerson
(74) Attorney, Agent, or Firm—Bacon & Thomas, PLLC

(57) ABSTRACT

The invention relates to a perineum muscular power increase device and a method wherein a user can do perineum shrink training continuously with interest and goal because the shrink and the relaxation degree of the perineum muscles may be displayed visually. According to the invention, there is provided with a muscular power increase device for perineum region comprising a pressure assembly 2 which presses the perineum muscle P of a sitter upwardly and makes the center of the perineum region pressed upwardly, a first detection means 53 which is provided at the pressure assembly 2 and detects the force or the pressure that the pressure assembly 2 is pushed downwardly by the shrink force of the perineum muscle P while the user is shrinking the perineum muscle P.

15 Claims, 10 Drawing Sheets

PERINEUM MUSCULAR POWER INCREASE DEVICE AND A METHOD THEREOF

FIELD OF THE INVENTION

The invention relates to a perineum muscular power increase device and a method thereof, more particularly, relates to a perineum muscular power increase device and a method thereof wherein a user can do perineum shrink training continuously with interest and goal because the shrink and the relaxation degree of the perineum muscles may be displayed visually, and wherein the user may do the shrink training for perineum muscle sanitarily and conveniently because there is no need to insert a special implement into the anus or the vagina.

BACKGROUND OF THE INVENTION

In general, the muscle of a body is developed through shrink training. On the other hand, the muscle is loosened and degenerates if it is not shrunk and remains at the state of relaxation. Similarly, the muscles of a perineum may be developed through shrink training. However, the perineum muscle is loosened and degenerates in the end if it continues to be at the state of relaxation. As for the shrink training of the perineum muscle, many experts like Dr. Kegel of America and so on have argued that, if the muscles around the perineum is shrunk and relaxed repeatedly, many diseases, for example, erection deficiency, urinary incontinence, melancholia, impatience, climacteric symptom, migraine, and chronic constipation may be cured as well as sexual ability may be enhanced. And, they have introduced the shrink training of the perineum muscles as excellent way to overcome many diseases like the above. Further, recently, even ordinary persons who are not proficient in the medical field have appreciated the effect of the shrink training of the perineum muscle.

However, there is a problem that, when a person does the shrink training of the perineum muscle, the other muscles like the femur muscle and so on may be shrunk together so that the perineum muscle cannot be shrunk as mush as he/she wants. Accordingly, recently, in order to overcome the problem like the above, many devices for helping the shrink training of the perineum muscle have been introduced and used. According to these devices, the user may do shrink training for the perineum muscle by inserting a cone into the anus or the vagina and by shrinking the muscle of the portion pressed by the cone. However, these insertion type devices have the weak points that the user may feel uncomfortable in training as well as humiliated or filthy so that he/she does not like to use them. And, despite the above weak points, because the goods to replace the devices like the above have not been introduced until now, these insertion type implements have been utilized only for curing the urinary incontinence.

And, not only the perineum shrink training is too monotonous but also the user may not visually watch the shrink or the relaxation degree of the perineum muscle. Accordingly, because there is no choice but to do a monotonous training repeatedly only with his/her will, the user may not keep doing the training even if he/she knows that the shrink training is very helpful for health.

SUMMARY OF THE INVENTION

The invention is created to solve the above described problems and so the object of the invention is to provide a perineum muscular power increase device and a method thereof wherein a user may do shrink training for perineum muscle continuously with interest and a certain aim because the shrink and the relaxation degree of the perineum muscle may be displayed visually, and wherein the user can do the shrink training of the perineum muscle sanitarily and conveniently without inserting a special implement into the anus or the vagina.

According to a first aspect of the invention, there is provided with a perineum muscular power increase device comprising:

a pressure assembly 2 which presses the perineum muscle P of a sitter upwardly and makes the center of the perineum region pressed upwardly;

a first detection means 53 which is provided at the pressure assembly 2 and detects the force or the pressure that the pressure assembly 2 is pushed downwardly by the shrink force of the perineum muscle P while the user is shrinking the perineum muscle P;

a first display means 57 which is connected to the first detection means 53 and displays the force or the pressure applied to the pressure assembly 2 visually;

and wherein the shrink degree as well as the relaxation degree may be displayed visually through the first display part 57 during the shrink training for the perineum muscle P so that the sitter may watch the visually displayed degrees and may continuously do the shrink training with interest.

According to another aspect of the invention, there is provided with the perineum muscular power increase device wherein a controller 50 is provided between the first display means 57 and the first detection means 53.

According to another aspect of the invention, there is provided with the perineum muscular power increase device wherein a reset button 56 is connected to the controller 50 and the sitter may initialize the force data or the pressure data transmitted from the first detection means 53 by the reset button 56.

According to another aspect of the invention, there is provided with the perineum muscular power increase device wherein the pressure assembly 2 comprises:

a pressure head 20 which presses the perineum muscle of the sitter upwardly;

and a lifting means 30 which is connected to the pressure head 20 and moves it upwardly and downwardly.

According to another aspect of the invention, there is provided with the perineum muscular power increase device wherein the pressure head 20 is connected to the lifting means 30 by a hinge and it may be rotated upwardly and downwardly, and an angle adjustment means 20a is provided between the pressure head 20 and the lifting means 30 so that the front end or the base end of the pressure head 20 may be ascended or descended, and the angle of the pressure head 20 may be adjusted corresponding to the lifting means 30.

According to a second aspect of the invention, there is provided with a perineum muscular power increase device comprising:

a pressure assembly 2 which presses the perineum muscle P of a sitter upwardly and makes the center of the perineum region pressed upwardly;

a fluid chamber 60 which is provided at the pressure assembly 2 and is pressed downwardly by the shrink force of the perineum muscle P as the sitter shrinks the perineum muscle P;

and a second display means 71 which is connected to the fluid chamber 60 and displays the force or the pressure transmitted from the fluid chamber 60 visually.

According to another aspect of the invention, there is provided with the perineum muscular power increase device wherein the second display means 71 is a fluid pressure gauge 72 which displays visually the pressure of the fluid transmitted from the fluid chamber 60 by an indication needle 72*a*.

According to another aspect of the invention, there is provided with the perineum muscular power increase device wherein a pressure sensor 71*a* detecting the pressure of the fluid and a controller 50 connected to the pressure sensor 71*a* are provided between the second display means 71 and the fluid chamber 60.

According to another aspect of the invention, there is provided with the perineum muscular power increase device wherein a reset button 56 is connected to the controller 50 and the pressure data transmitted from the pressure sensor 71*a* may be initialized by the reset button 56.

According to another aspect of the invention, there is the perineum muscular power increase device wherein the second display means 71 comprises:

a cylinder 70 which is connected to the fluid chamber 60 and the piston 73 of which may be pushed by the pressure of the fluid transmitted from the fluid chamber 60;

an elasticity means 75 which is provided in the cylinder 70 and pushes the piston 73 elastically toward the inflow direction of the fluid;

and an indication needle 77 which is connected to the piston 73 and moves forwardly and backwardly to display the force or the pressure applied to the pressure assembly 2 visually.

According to a third aspect of the invention, there is provided with a perineum muscular power increase device comprising:

a pressure head 20 which presses the perineum muscle P of the sitter upwardly and makes the center of the perineum muscle pressed upwardly;

an elasticity means 28 which pushes the pressure head 20 upwardly;

a second detection means 53*a* which is provided under the pressure head 20 and detects the descending distance of the pressure head 20 or detects whether the pressure head 20 is contacted thereto by the shrink force of the perineum muscle P as the user shrinks the perineum muscle P;

a third display means 80 which is connected to the second detection means 53*a* and displays the detected data visually.

According to another aspect of the invention, there is provided with a perineum muscular power increase device wherein the third display means 80 comprises:

a controller 50 where a signal of the second detection means 53*a* is inputted;

and a third displayer 81 which is connected to the controller 50 and displays the detected data visually.

According to another aspect of the invention, there is provided with the perineum muscular power increase device wherein a controller 50 is provided between the third display means 80 and the second detection means 53*a*.

According to a forth aspect of the invention, there is provided with a perineum muscular power increase device comprising:

a pressure head 20 which presses the perineum muscle P of the sitter upwardly;

a lifting means 30 which is connected to the pressure head 20 and moves it upwardly and downwardly;

an elasticity means 28 which pushes the lifting means 30 upwardly;

a second detection means 53*a* which is provided under the lifting means 30 and detects the descending distance of it or whether the lifting means 30 is contacted thereto by the shrink force of the perineum muscle P as the user shrinks the perineum muscle P;

a third display means 80 which is connected to the second detection means 53*a* and displays the detected data visually.

According to another aspect of the invention, there is provided with the perineum muscular power increase device wherein a controller 50 is provided between the third display means 80 and the second detection means 53*a*.

According to a fifth aspect of the invention, there is provided with a perineum muscular power increase device comprising:

a pressure assembly 2 which presses the perineum muscle P of the sitter upwardly and makes the center of the perineum muscle P pressed upwardly;

an elasticity means 28 which pushes the pressure assembly 2 upwardly;

a forth display means 88 having an indicator 85 which is connected to the pressure assembly 2 and is moved together with the pressure assembly 2 to display the descending distance of the pressure assembly 2 visually as the sitter shrinks the perineum muscle P.

According to a sixth aspect of the invention, there is provided with a perineum muscular power increase method comprising:

a step in which the sitter makes the perineum muscle P pressed by the pressure assembly 2;

a step in which the sitter shrinks the pressed perineum muscle P in order that the pressure assembly 2 be pushed toward the opposite direction of the pressing direction;

and the shrink training for the perineum muscle may be done conveniently only if the sitter shrinks the portion pressed by the pressure assembly 2 and makes the pressure head pushed toward the pressing direction.

According to another aspect of the invention, there is provided with the perineum muscular power increase method further comprising;

a step in which the force or the pressure pushing the pressure assembly 2, or the retreat of the pressure assembly 2 is detected while the sitter shrinks the perineum muscle P;

and a step in which the detected data is displayed visually.

DETAILED DESCRIPTION OF THE INVENTION

A preferred embodiment of the invention will be described in detail below by referring to the accompanying drawings.

Figure 1:
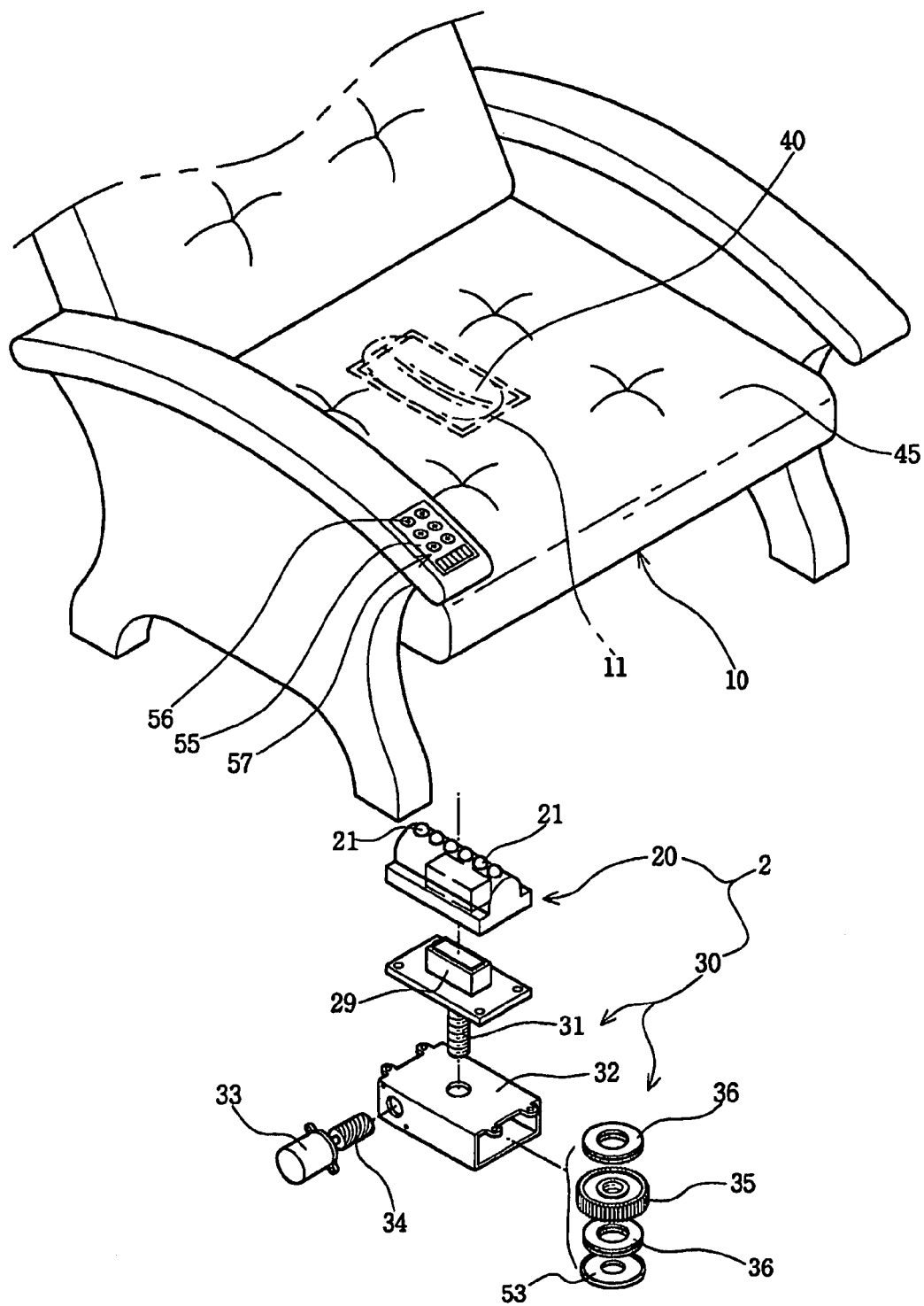
FIG. 1 is a dissembled perspective view of a first embodiment of the invention.
Figure 2:
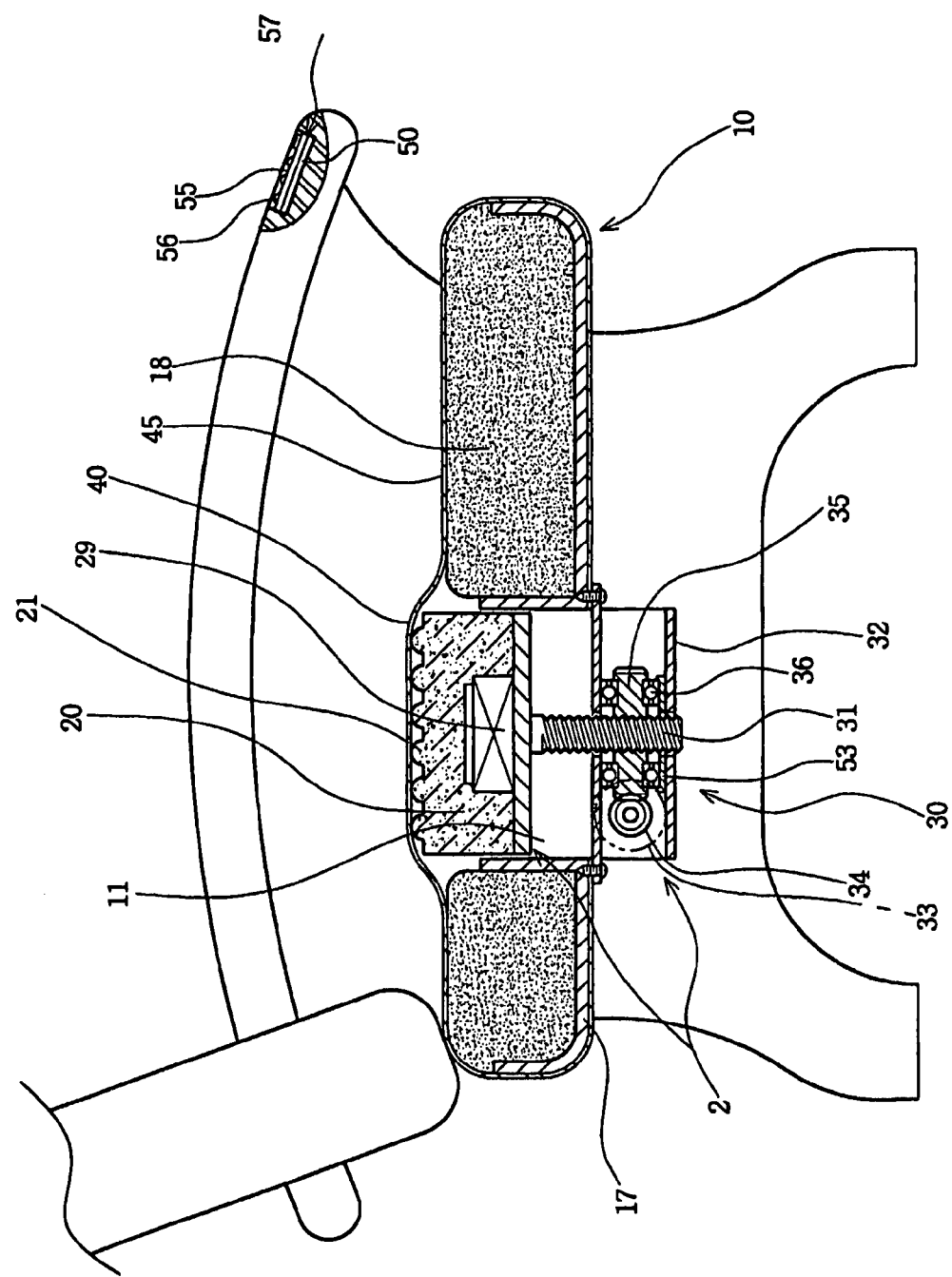
FIG. 2 is the assembled sectional view of FIG. 1.

FIG. 1 and FIG. 2 are respectively the dissembled perspective view and the sectional view of a first embodiment of the invention. Referring to the drawings, the first embodiment of the invention includes a pressure assembly 2 which is provided in the seat part 10 of a chair and presses the perineum region of the sitter upwardly, a first detection means 53 which is provided at the pressure assembly 2 and detects the force or the pressure applied to the pressure assembly 2 as the sitter shrinks the perineum muscle P of FIG. 10, and a first display means 57 which is connected to the first detection means 57 and displays the force or the pressure detected by the detection means 57. Here, The pressure assembly 2 includes a pressure head 20 which presses the perineum region of the sitter upwardly, and a lifting means 30 which moves the pressure head 20 upwardly and downwardly.

The seat part 10, as shown in FIG. 2, includes a cushion member 18 mounted on a seat frame 17, and a main cover 45 which covers the cushion member 18. Here, an opening 11 perforated from the upper surface to the lower surface is provided at the center of the seat part 10, and the centers of the cushion member 18 and the main cover 45 are cut to be opened in the same shape as that of the opening 11 so that the pressure head 20 may be ascended and descended through the opening 11. And, a subsidiary cover 40 is provided on the upper side of the opening 11 and the pressure head 20 is covered with the subsidiary cover 40. Here, the subsidiary cover 40 is preferably provided on the opening 11 as loose sheet cover 45 or the subsidiary cover 40 is made of more elastic material than that of the main cover 45 in order that the pressure head 20 may be readily ascended when it ascends toward the upper side of the seat part 10.

The pressure assembly 2 may be composed of only a pressure head 20 which presses the perineum region of the sitter upwardly. And, as shown in the drawings, the pressure assembly 2 may be mounted on the upper part of the lifting means 30 and may be moved upwardly and downwardly by the lifting means 30. Here, a vibration motor 29 is provided in the pressure head 20 so that the perineum muscle of the sitter may be massaged vibratingly by the vibration motor 29. And, a plurality of pressure projections 21 are provided on the upper surface of the pressure head 20 so that the perineum region of the sitter may be massaged more effectively by the projections 21. Further, a magnet (not shown in the drawings) is provided in the pressure head 20 so that the blood of the perineum region may be circulated more readily.

Figure 3:
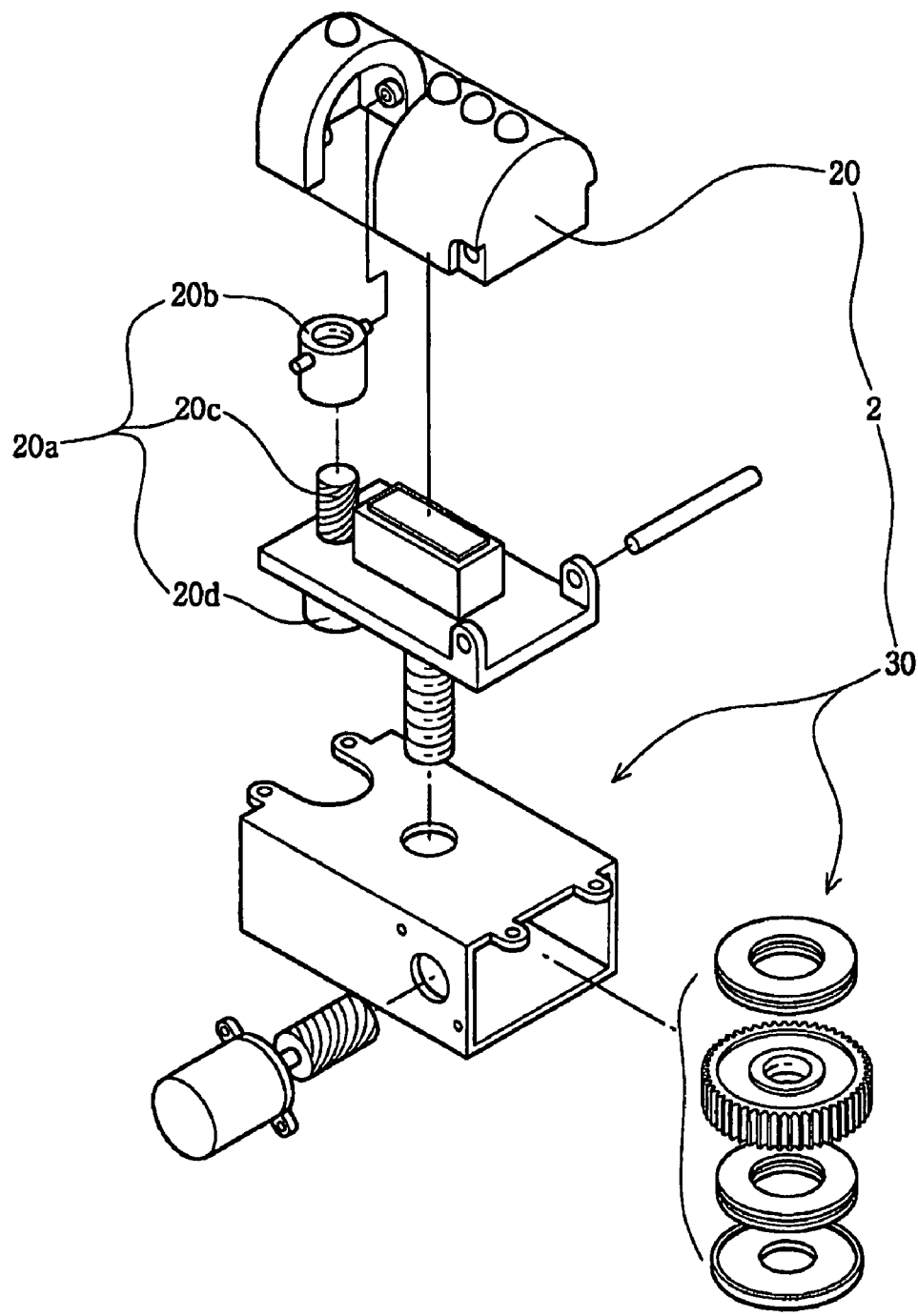
FIG. 3 is the dissembled view of an angle adjustment means of the invention.

Here, the pressure head 20 may be fixed on the upper end of the lifting means 30, however, as shown in FIG. 3, it may be connected to the upper end of the lifting means 30 through a hinge and an angle adjustment means 20*a* may be provided between the pressure head 20 and the lifting means 30 so that the sitter may adjust the angle of the pressure head 20 corresponding to the lifting means 30 and use the device of the invention conveniently. The angle adjustment means 20*a* may be composed of a jack nut 20*b* connected to the pressure head 20, a subsidiary motor 20*d* provided at the lifting means 30 vertically, and a jack screw 20*c* which is provided at the shaft of the subsidiary motor 20*d* and is connected to the jack nut 20*b*. Further, although not shown in the drawings, like as an embodiment that a wedge block is pushed to be inserted between the pressure head 20 and the lifting means 30, an embodiment that the front end or the base end of the pressure head 20 is lifted by a cam or an embodiment that the hinge combination part of the pressure head 20 is rotated by a worm, various kinds of the embodiments may be adopted to the invention if they are provided between the pressure head 20 and the lifting means 30 and may make the angle of the pressure head 20 adjusted conveniently.

Preferably, the angle adjustment means 20*a* is provided in the pressure assembly 2 and the sitter can adjust the angle of the pressure head 20 conveniently through the angle adjustment means 20*a* according to the sitting pose. In this case, if the sitter lays his/her upper body toward the backward side and the perineum region becomes relatively lower than the front side of the perineum region, he/she may accord the angle of the pressure head 20 to that of the perineum region by lowering the backward side of the pressure head 20 and may use the device of the invention conveniently. Further, if the angle adjustment means 20*a* is provided in the pressure assembly 2 like the above, the training effect for the specific position of the perineum region may be increased because the sitter may do the shrink train for the perineum region at the state that the front position or the back position of the perineum region is pressed by the pressure head 20 relatively more.

The lifting means 30, as shown in FIG. 2, makes the perineum region of the sitter pressed or massaged by moving the pressure head 20 upwardly. And, the lifting means 30 moves the pressure head 20 downwardly so that the perineum region of the sitter is not pressed although the user takes a seat for a long time. The lifting means 30 may adopt all the embodiments that the pressure head 20 may be moved upwardly and downwardly like as the embodiment that it is ascended and descended by a motor and a screw shaft or by a solenoid, a cylinder or a link.

The typical lifting means is to utilize a motor and a screw shaft. According to this means, the lifting means 30 includes a bracket 32 fixed at the lower surface of the seat part 10, a screw shaft 31 which is fixed at the lower surface of the pressure head 20 and is provided at the bracket 32 vertically, and a motor 33 which is connected to the screw shaft 31 and moves the pressure head 20 upwardly and downwardly.

And, a worm 34 is mounted at the shaft of the motor 33 and a worm gear 35 is mounted at the screw shaft 31 so that the worm 34 and the worm gear 35 are engaged each other. The worm gear 35 is supported upwardly by the bracket 32. Accordingly, if the worm gear 35 is rotated, the screw shaft 31 is moved upwardly and downwardly. And, a bearing 36 and a first detection means 53 (described below) are provided between the worm gear 35 and the bracket 32 in order to decrease friction.

And, it is possible that the screw shaft 31 is rotated by the motor at the state of being supported by the bracket 32 and the pressure head 20 is rotatably combined at the periphery of the screw shaft 31. In this case, the pressure head 20 is moved upwardly and downwardly when the screw shaft 31 is rotated by the motor 33.

Further, preferably, the motor 33 is connected to a controller 50 (described below) in order that the rotation angle of it may be controlled, and the controller 50 is connected to the input means 55 in order that a signal may be inputted to it, and operation program for each mode is previously stored to the controller 50. In this case, the motor 33, the vibration motor 29, and a first display part 57 and so on may be operated according to the program when a certain operation mode is chosen through the input part 55.

Figure 10:
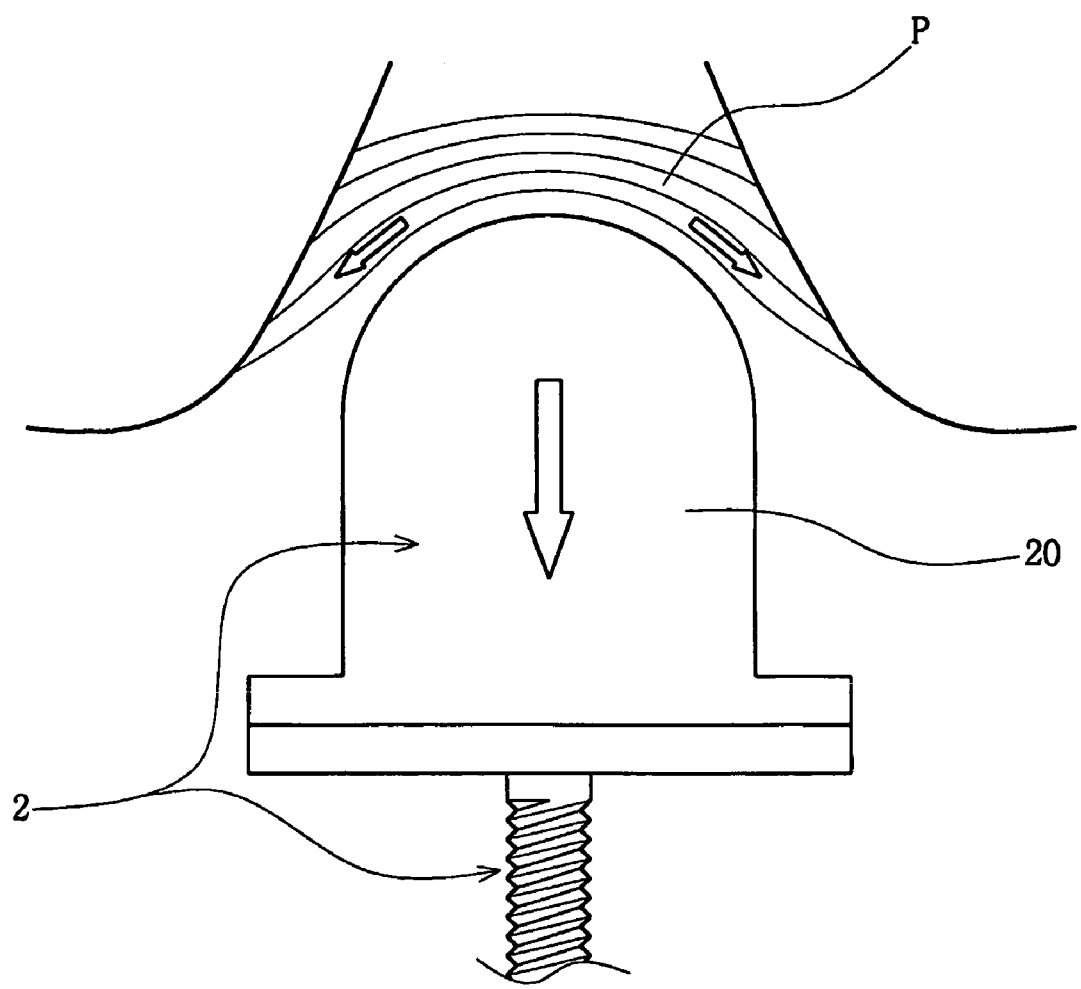
FIG. 10 is a sectional view showing the operation state of the invention.

Accordingly, if the pressure head 20 is ascended by the lifting means 30, as shown in FIG. 10, the center of the perineum muscle P is pushed to be ascended upwardly, and if the sitter shrinks the perineum muscle P at such a state, the perineum muscle P pushed to be ascended upwardly is stretched downwardly so that the pressure head 20 is moved downwardly. Here, a first detection means 53 is provided in the lifting means 30 of FIG. 2 and may be shrunk vertically so that the shrink force which moves the pressure head 20 downwardly is detected by the first detection means 53 and the shrink force may be displayed visually.

For example, the first detection means 53 is provided between the bracket 32 and the worm gear 35 so that it detects the shrink pressure or the shrink force of the perineum muscle P, and the detected data is transmitted to a first display means 57 so that it is visually displayed by a LED or a digital display means. Here, the first detection means 53 may be provided between an upper pressure head and a lower pressure head which have been divided into a pair, or it may be provided between the pressure head 20 and the lifting means 30. Like this, the first detection means 53 may be provided wherever the force or the pressure applied to the pressure head 20 is transmitted while the sitter is shrinking the perineum region.

Further, when the perineum region is shrunk, the first detection means 53 detects the pressure or the force applied to the perineum region and makes the force or the pressure displayed visually through the first display part 57. Accordingly, the sitter may adjust the pressure or the force of the pressure assembly 2 to the degree suitable for him/her.

The first display means 57 displays the force data or the pressure data transmitted from the first detection means 53 visually. Preferably, the controller 50 of FIG. 2 is connected between the first detection means 53 and the first display means 57. In this case, the force data or the pressure data transmitted from the first detection means 53 may be displayed in a variety of types like as in a digitalized type. Of course, without the controller 50 at the display means 57, it is possible that the data from the first detection means 53 may be transmitted to the first displayer 57a through an amplifier and etc that the data may be displayed as analogue signal.

Preferably, a reset button 56 is connected to the controller 50 so that the force or the pressure data transmitted from the first detection means 53 may be initialized as zero if the sitter pushes the reset button 56. Accordingly, if the sitter pushes the reset button 56 and shrinks his/her perineum region, the weight of the sitter applied to the pressure assembly 2 is excluded and only the force or the pressure during the shrink of the perineum region is displayed visually.

And, according to the embodiment, the pressure assembly 2 is mounted at the seat part 10 of a chair. However, it is also possible that the pressure assembly 2 is not mounted at the seat part 10 but is manufactured in an independent unit. In this case, after taking down the pressure assembly 2 on the floor of a room and sitting on it, the user may do the shrink train for the perineum muscle P, watching the degree of the shrink or the relaxation of the perineum muscle P through the first display means 57.

According to the first embodiment of the invention as described above, when the pressure head 20 has been moved upwardly and the perineum muscle P of FIG. 10 has been pushed to be moved upwardly, if the sitter shrinks the perineum muscle P, the pressure head 20 is moved downwardly by the shrink force of the perineum muscle P so that the force or the pressure is detected by the first detection means 57 of FIG. 2 while the sitter is shrinking the perineum muscle P and it is displayed visually by the first display part 57.

Further, the pressure head 20 is moved upwardly by the lifting means and the perineum region of the sitter is pressed by it so that the pressure or the massage may be applied at the same time. Here, the first detection means 57 is provided at the pressure assembly 2 and makes the force or the pressure displayed visually while the perineum region is being pressed or massaged by the sitter's shrink training. Accordingly, the sitter may adjust the force or the pressure to the degree most suitable for him/her.

The operation of the first embodiment will be described below in each mode by referring to FIG. 2 and FIG. 10. Firstly, if the sitter inputs the massage mode through the input part 55, the pressure head 20 is ascended by the lifting means 30 and makes the perineum region of the sitter pressed upwardly as well as the vibration motor 29 is driven to massage the perineum region by vibration so that the fatigue accumulated to the perineum region may be dissolved.

And, the sitter inputs the pressure mode, the pressure head 20 is moved upwardly by the lifting means 30 and the perineum region is pressed toward the upper direction upwardly for a predetermined time. And, the pressure head is again moved downwardly and release the pressure. As a result, because the pressure head 20 repeats ascending and descending movement continuously so that the perineum region may be pressed and relaxed repeatedly for a predetermined time, the acupuncture point around the perineum region may be pressed as if the acupuncture point is pressed by a finger pressure professional. Accordingly the pressure effect may be acquired that the circulation organism is normally recovered or the circulation function may be enhanced.

Next, if the sitter inputs the training mode, the pressure head 20 is moved upwardly by the lifting means 30, as shown in FIG. 10, the central part of the sitter's perineum region is pushed upwardly to be maintained at the state. And, if the sitter shrinks the perineum muscles P at this state, the perineum muscles P pushed upwardly is pulled downwardly again. Here, a first detection means 53 is provided in the lifting means 30 vertically, and the descending pressure or force of the pressure head 20 may be detected by the first detection means 30 to be transmitted to a controller 50 so that the controller 50 displays the data inputted from the first detection means 30 visually. Accordingly, the sitter may continue the shrink training with interest, watching the shrink and the relaxation degree of the perineum region. And, a timer (not shown) is preferably provided in the controller 50. Accordingly, the first display means 57 displays the time for which the perineum muscles P is shrunk, the sitter may do the shrink training after exactly adjusting the time of the shrink and the relaxation.

Figure 4:
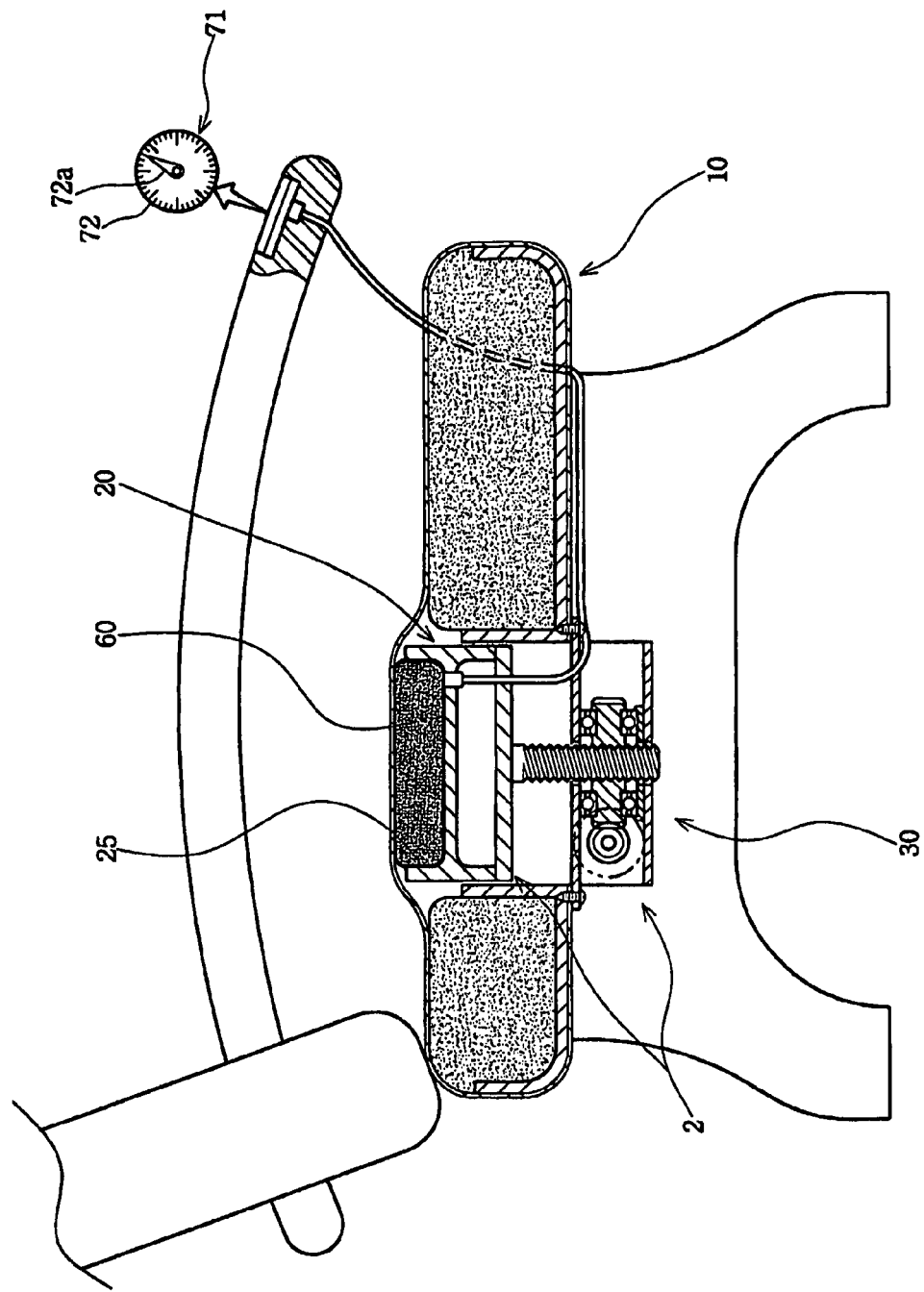
FIG. 4 is a sectional view of a second embodiment of the invention.

And, a second embodiment of the invention, as shown in FIG. 4, includes a pressure assembly 2 which is provided at the center of the seat part 10 and is projected upwardly, a fluid chamber 60 provided in the pressure assembly 2, and a second display part 71 which is connected to the fluid chamber 60 and displays the pressure of the fluid transmitted from the fluid chamber 60.

Here, the pressure assembly 2 includes a pressure head 20, and a lifting means 30 which moves the pressure head 20 upwardly and downwardly. And, the seat part 10, the pressure head 20, and the lifting means 30 are as same as those of the first embodiment, and the detailed description for these will not be explained below.

The fluid chamber 60 is provided in the pressure assembly 2, and it is composed of a fluid chamber and so on. And, the inner space of the fluid chamber 60 is filled with fluid. Accordingly, when the sitter shrinks the perineum muscles P, the fluid chamber 60 is pressed downwardly so that the fluid in the chamber 60 is transmitted to the second display means 71. The fluid chamber 60 may be provided wherever the shrink force of the perineum muscle P may be transmitted. Preferably, a groove 25 is provided on the upper surface of the pressure head 20, and the fluid chamber 60 is provided in the groove 25. In this case, the fluid chamber 60 may be also functioned as a cushion member.

The second display means 71 adopts the conventional fluid pressure gauge 72 which displays the pressure of the fluid transmitted from the fluid chamber 60 by an indication needle 72a visually.

The seat part 10 described above may be adopted not only to the seat panel of a chair but also a cushion or a variety of seat panels to sit on. And, the pressure assembly 2 includes not only the case that the pressure head 20 is moved up and down by the lifting means but also the case that the pressure head 20 is always projected from the upper surface of the seat panel without a specific lifting means. Further, not only the pressure assembly 2 is provided in the seat part 10 but also it may be manufactured in an independent unit. In this case, after he/she takes down the pressure assembly 2 on the floor of a room and sits on it, the sitter may do the shrink train for the perineum P, watching the degree of the shrink or the relaxation degree of the perineum muscle P through the first display means 71.

Figure 5:
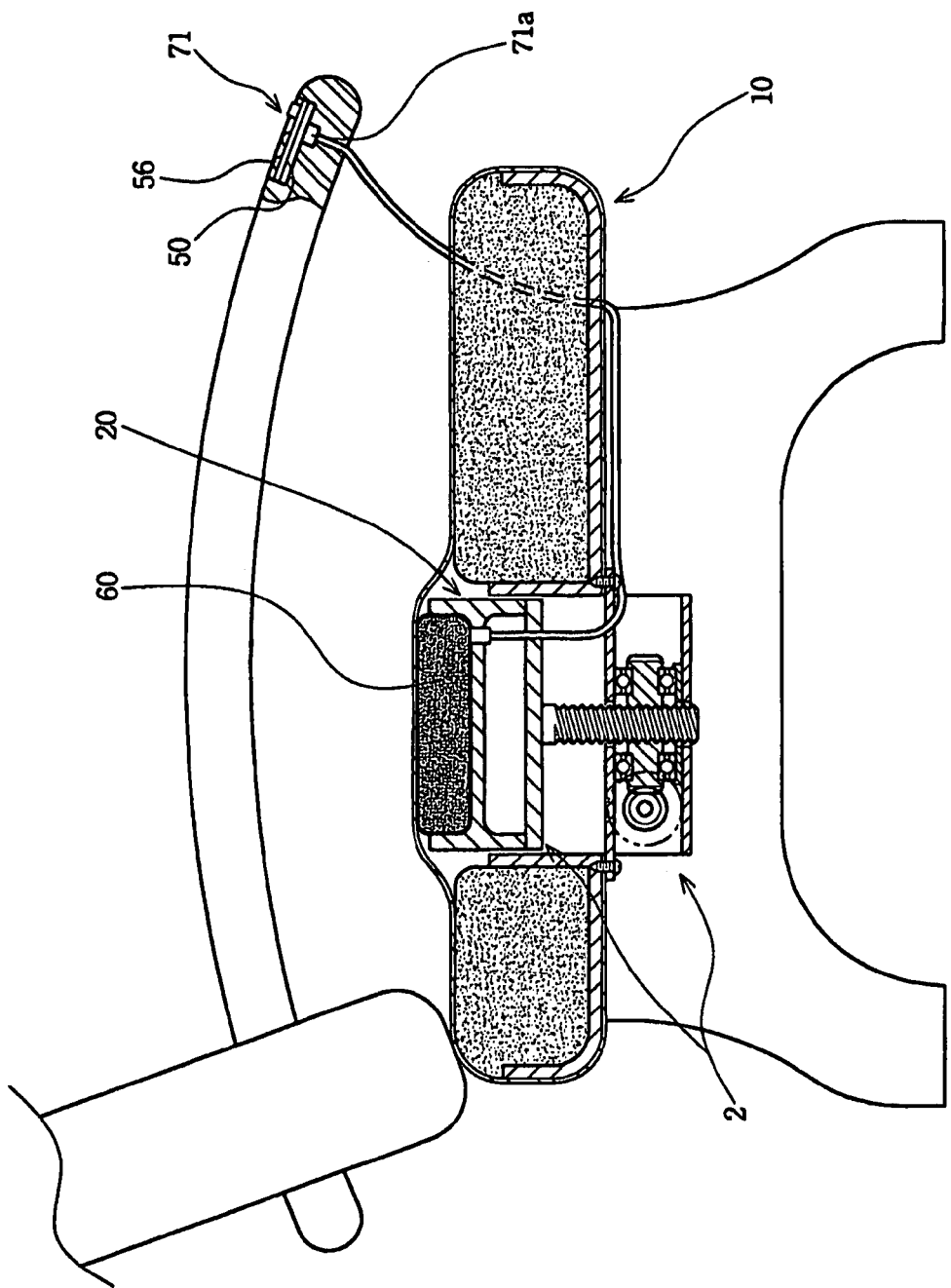
FIG. 5 is a first application example of the second embodiment.

And, FIG. 5 shows a first application example of the second embodiment. The seat part 10, the pressure assembly 2, and the fluid chamber 60 and so on of the first application example are as same as those of the above described second embodiment. However, a pressure sensor 71a and a controller 50 are further connected between the fluid chamber 60 and the second display means 71. The controller 50 converts a signal transmitted from the pressure sensor 71a into data(for example, figure data) and transmits the data to the second display means 71.

Here, as described in the first embodiment, a reset button 56 is connected to the controller 50. The reset button 56 initializes the pressure data transmitted from the pressure sensor 71a as zero value. Further, as described in the first embodiment, the program for pressure, massage and training is previously stored in the controller 50 so that the sitter may select the desired mode and use the device of the invention.

The training mode of the first application example of the second embodiment is as follows. If the sitter shrinks the perineum muscles P of FIG. 10 at the state that the perineum region has been pushed upwardly and is ascended by the pressure head 20, the fluid chamber 60 is pressed downwardly by the shrink force of the perineum P so that the fluid in the fluid chamber 60 (for, a fluid chamber) is transmitted to the second display means 71 and this second display means 71 displays the pressure applied to the fluid chamber 60 visually. Accordingly, the sitter may continue the shrink for the perineum muscle P interestingly, watching the shrink or the relaxation degree of the perineum muscle P.

Figure 6:
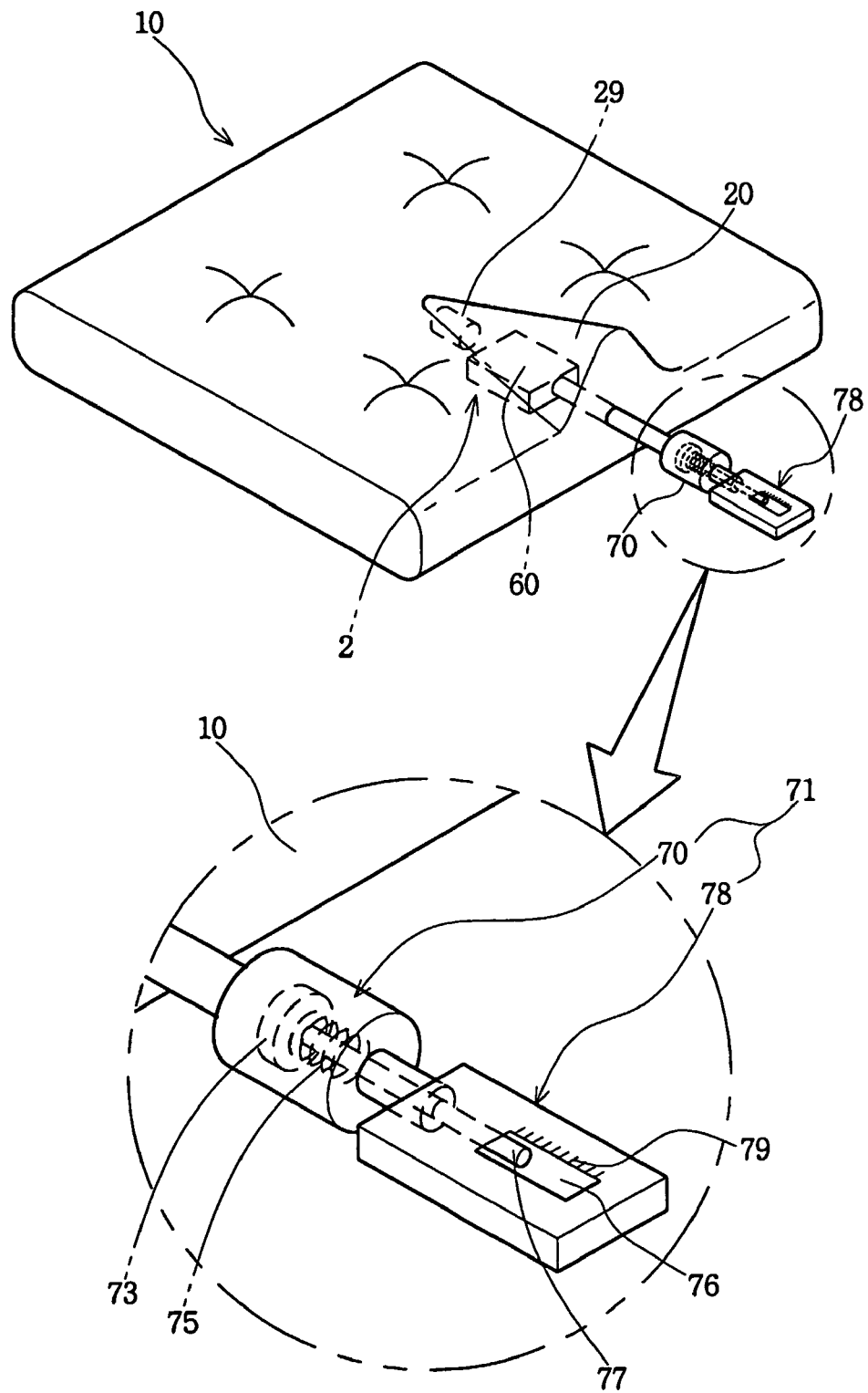
FIG. 6 is a second application example of the second embodiment.

And, FIG. 6 shows a second application example of the second embodiment, which includes a pressure assembly 2 which is projected upwardly at the center of the seat part 10, a fluid chamber 60 provided in the pressure assembly 2, and a second display means 71 which is connected to the fluid chamber 60 and displays the pressure of the fluid transmitted from the fluid chamber 60. Here, the second display means 71 is composed of a cylinder 70 which is expanded or contracted by the pressure of the fluid transmitted from the fluid chamber 60, an elasticity means 75 which pushes the piston 73 in the cylinder 70 against the inflow direction of the fluid, and a display means 78 having an indication needle 77. The indication needle 77 is moved forwardly or backwardly by the piston 73 and displays the pressure applied to the pressure assembly 2 while the sitter is shrinking the perineum muscle P.

And, the pressure assembly 2 includes a pressure head 20 which is projected upwardly at the center of the seat part 10 and presses the perineum region of the sitter upwardly. The pressure head 20 is composed of elastic material, and a fluid chamber 60 is provided in the pressure head 20. And, a vibration motor 29 is mounted in the pressure head 20 and the perineum region of the sitter may be vibrated and massaged by the vibration motor 29. Accordingly, the fluid chamber 60 like as a fluid pack is pressed downwardly by the shrink force of the perineum muscle P when the sitter shrinks the perineum region so that the fluid in the fluid chamber 60 is transmitted to the cylinder 70.

The cylinder 70 is to be extended when its piston 73 is pushed backwardly by the pressure of the fluid transmitted from the fluid chamber 60. And, an elasticity means 75 is provided in the cylinder 70 and the piston 73 is pushed toward the shrink direction of the cylinder 70.

The display means 78 has an indication needle 77 which is connected to the piston 73. Here, the forward end of the piston 73 may be utilized as the indication needle 77, or a needle may be provided at the forward end of the piston 73. And, a transparent gaze panel 76 is provided at the display means 78 in order that the sitter may see through the indication needle 77, and a scale 79 is marked at the outer surface of the gaze panel 76 or the indication implement 76.

The training mode of the second application example of the second embodiment is as follows. If the sitter shrinks the perineum muscles P of FIG. 10 at the state that the perineum region has been pushed upwardly and ascended by the pressure head 20, the fluid chamber 60 is pressed downwardly by the shrink force of the perineum muscle P so that the fluid filled in the pack 60 is forcibly transmitted to the cylinder 70. Accordingly, the piston 73 of the cylinder 70 is pushed backwardly by the pressure of the fluid which flows in the cylinder 70 so that the pressure applied to the fluid chamber 60 may be displayed by the indication needle 77 connected to the piston 73.

And, if the perineum muscle P is relaxed again, the pressure applied to the fluid chamber 60 is released and the piston 73 in the cylinder 70 is pushed backwardly by the repelling force of the elasticity means 75 so that the fluid flown in the cylinder 70 is transmitted into the fluid chamber 60 again and the indication needle 77 connected to the piston 73 is restored to the original state.

Figure 7:
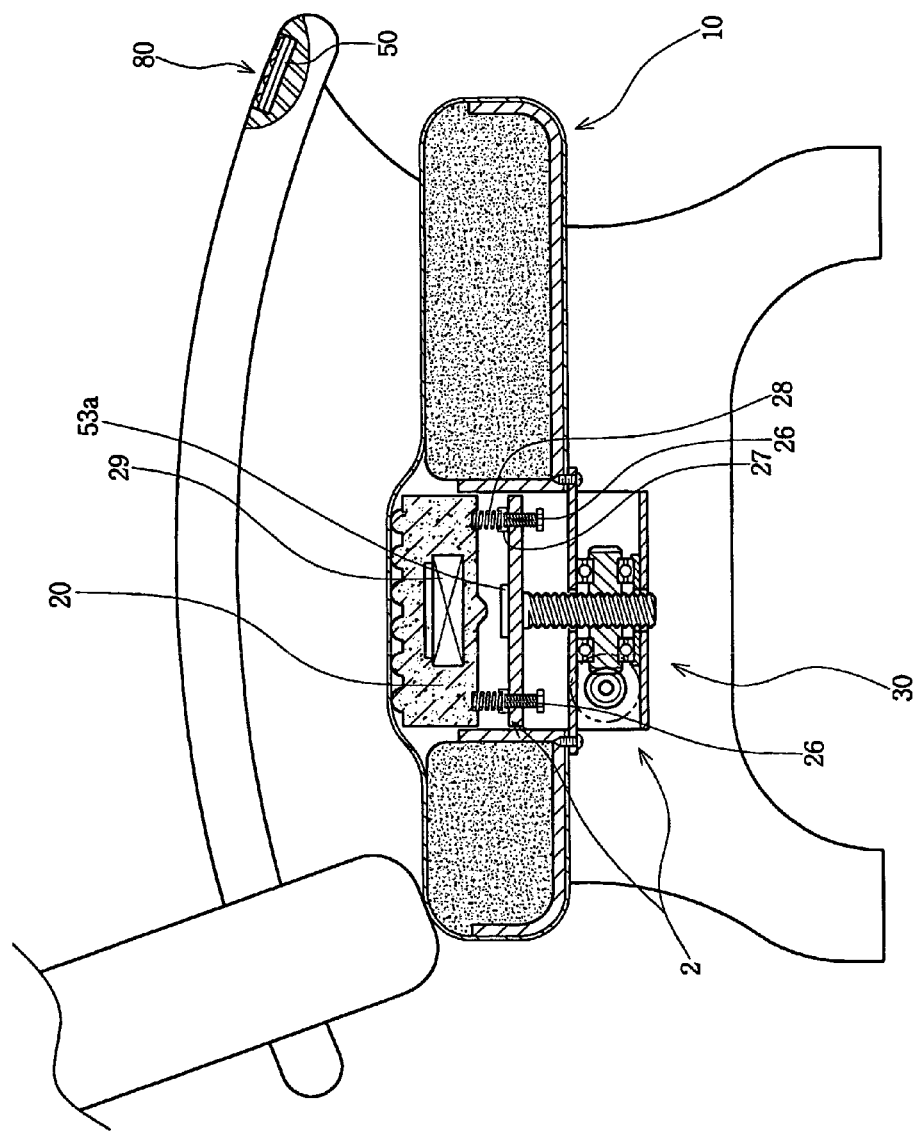
FIG. 7 is a sectional view of a third embodiment of the invention.

Further, a third embodiment of the invention, as shown in FIG. 7, includes a pressure head 20 which is provided in the center of the seat part 10 and presses the perineum region of the sitter upwardly, an elasticity means 28 which pushes the pressure head 20 upwardly, a second detection means 53a which is provided under the pressure head 20 and detects the descending distance of the pressure head 20 or whether the pressure head 20 is contacted thereto when the sitter shrinks the perineum region, and a third display means 80 which is connected to the second detection means 53a and displays the detected data visually.

The pressure head 20 is provided over the same lifting means 30 to that described in the above described first embodiment in order to be elastically pushed upwardly, or, although not shown, it is provided in the seat part 10 in order to be elastically pushed toward the upper direction by the elasticity means 28. And, a vibration motor 29 is provided in the pressure head 20.

The elasticity means 28 is vertically provided on the washer 27 which is moved upwardly or downwardly by a adjustment screw 26, and pushes the adjustment screw 26 elastically toward the upper direction. And, as needed, the sitter may adjust the elastic force of the elasticity means 28 by tightening or by loosening the adjustment screw 26.

The second detection means 53*a* is provided under the pressure head 20. If the sitter shrinks the perineum muscles P, the second detection means 53*a* detects the distance that the pressure head is moved up and down by the shrink force of the perineum muscles P or whether the pressure head 20 is contacted thereto. The second detection means 53 may adopt a proximity sensor, a touch sensor, or many kinds of sensors including a switch which may detect the moving distance of the pressure head 20 or whether the pressure head 20 is contacted thereto.

The third display means 80 displays the data detected by the second detection means 53*a* visually. Preferably, a controller 50 is connected between the second detection means 53*a* and the third display means 80. Here, the controller 50 may have pressure mode, massage mode and training mode so that the sitter may select the respective modes that he/she wants.

Further, it is also possible that a timer(not shown) is provided in the controller 50. In this case, if a signal from the second detection means 53*a* is inputted into the controller, the third display means displays the time that the perineum muscle P is shrunk so that the user may know whether the perineum muscle P is shrunk or not. Further, a specific controller is not provided between the second detection means 53*a* and the third display means 80 but a lamp is provided at the third display means 80 and the lamp may be lighted by the signal 'ON' of the second detection means 53*a*.

The training mode of the third embodiment is as follows. If the sitter shrinks the perineum muscles P of FIG. 10 at the state that the perineum region has been pushed upwardly and is ascended by the pressure head 20, the shrink force of the perineum muscles P is applied to the pressure head 20 and the pressure head is descended downwardly against the elastic force of the elasticity means 28. Here, the second detection means 53*a* is provided under the pressure head 20 and the second detection means 53*a* detects the distance that the pressure head 20 is moved up and down or whether the pressure head 20 is contacted thereto so that the distance data or the shrink signal may be displayed visually by the third display means 80. Accordingly, the sitter may do continuously the shrink training with interest, watching the shrink degree of the perineum muscles P through the third display means 80.

Figure 8:
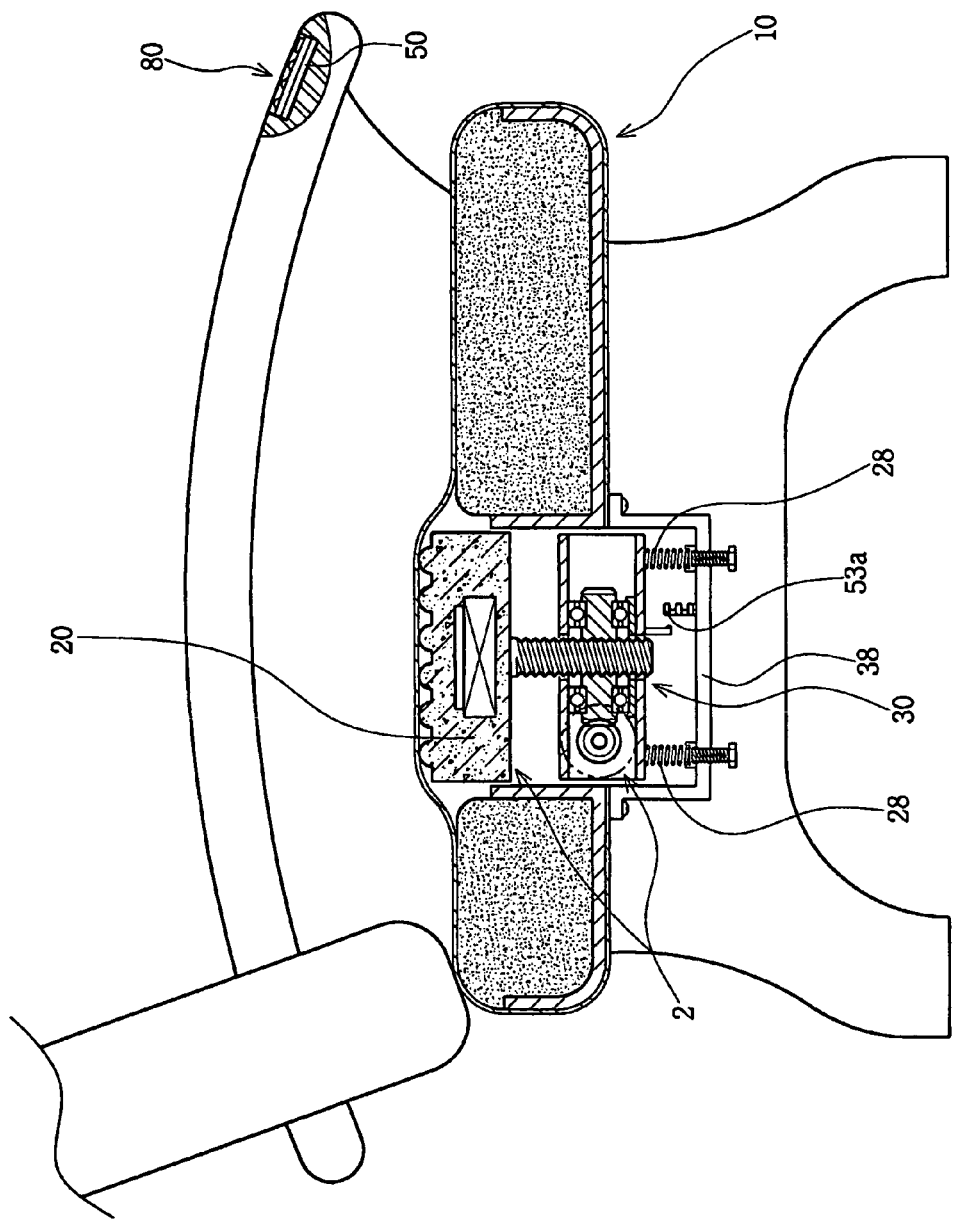
FIG. 8 is an application example of the third embodiment.

Further, FIG. 8 shows the application example of the third embodiment. And, as the pressure head 20, the lifting means 30, the second detection means 53*a*, the third display means 80 and so on are as similar as those of the above described third embodiment, the detailed for these will not be described below. However, according to this application example, a channel type support bracket 38 is provided at the lower surface of the seat part 10, a pressure assembly 2 having a pressure head 20 and an lifting means 30 is provided on the upper surface of the support bracket 38, and a second detection means 53*a* is provided at the lower side, that is, on the upper surface of the support bracket 38. And, the second detection means 53*a* detects the descending distance of the pressure assembly 2 or whether the pressure assembly 2 is contacted thereto.

Figure 9:
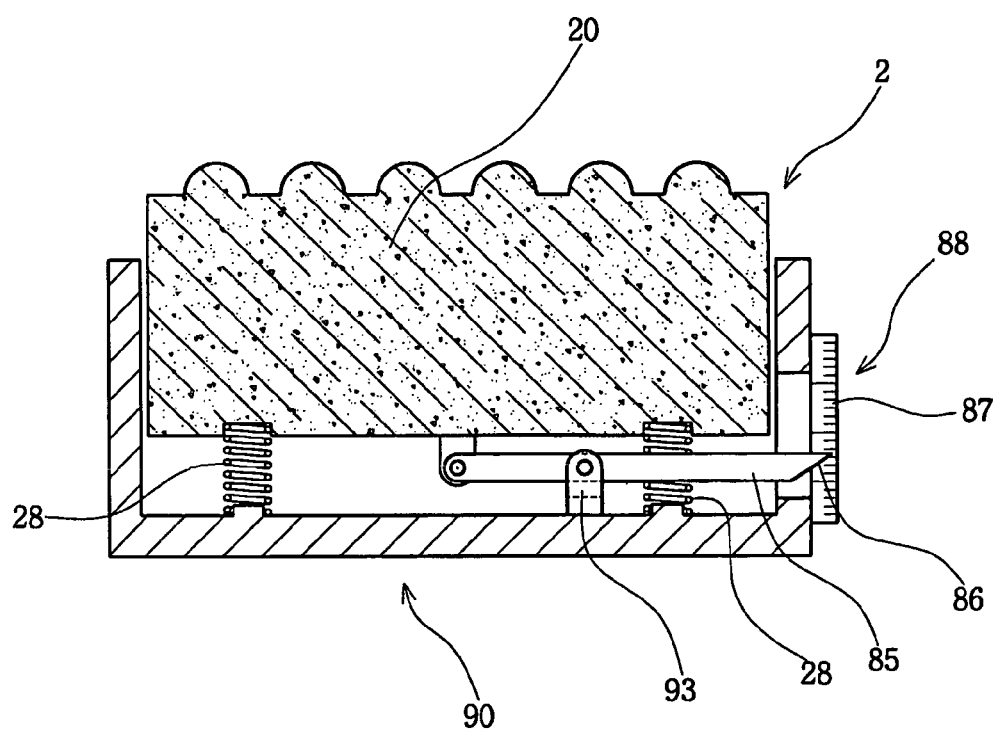
FIG. 9 is a sectional view of a forth embodiment of the invention.

Further, a forth embodiment of the invention, as shown in FIG. 9, comprises a pressure assembly 2 which is provided in a housing 90, an elasticity means 28 which elastically pushes the pressure assembly 2, and a forth display means 88 having an indicator 85 which is connected to the pressure assembly 2 and displays the descending distance of the pressure assembly 2 while the perineum muscle P is shrunk. Here, the pressure assembly 2 may be composed of only a pressure head 20, or may be composed of both the pressure head 20 and the lifting means 30 as shown in FIG. 8. And, the pressure assembly or the elasticity means and so on is similar to those of the above described first embodiment, the detailed description for these will not be explained below.

The indication gauge 85 is a lever whose central part is combined to the bracket 93 in the housing 90 by a hinge in order to be rotated upwardly and downwardly as axis at the hinge, and one end of it is connected to the pressure head 20 rotatably and the visually exposed indication means 86 is provided at another end of it. Here, the indication means 86 is covered with a transparent gaze window (or, panel) 87 and a scale is marked on the transparent window 87 so that the sitter may watch the descending degree of the pressure head 20. Further, the indicator 85 may adopt whatever may be moved together with the pressure head 20 when the pressure head 20 is descended and operate the visually exposed indicator 85.

The training mode of the forth embodiment will be explained below. If the sitter shrinks the perineum muscles P at the state that the perineum region has been pushed upwardly and is ascended by the pressure head 20, the pressure head 20 is descended against the elastic force of the elasticity means 28 by the shrink force of the perineum muscle P. Here, the pressure head 20 is connected to one end of the indicator 85 by a hinge and one end of the indication implement 85 is descended together with the pressure head 20 so that the indicator 86 provided at another end of the indicator 85 is ascended toward the opposite direction and displays the shrink force of the perineum muscle P.

In the above embodiments, the components described in the same terms and the same references have been explained briefly in order to prevent the redundant explanation, however, it must be noted that all of these components have the same structure and the same function to those described in the above embodiments.

Further, the method of increasing the shrink force of the perineum muscle P has been described in respective training modes of the respective embodiments, but the method will be briefly described below. Firstly, when the perineum region of the sitter is pressed upwardly by the pressure assembly 2 of FIG. 10 and the center of the perineum muscle P is pushed upwardly, if the sitter shrinks the perineum muscle P and makes the pressure assembly 2 pressed downwardly, the user may do the shrink training for the perineum muscle P conveniently and effectively without inserting a specific implement into the anus or the vagina.

And, the force or the pressure or the descending distance applied to the pressure assembly 2 is detected through the respective detection means 53, 53*a*, the pressure sensor 71*a*, the pressure means 72 or the pressing degree of the elasticity means 28, 75 to be displayed visually.

And, according as the sitter shrinks the perineum muscle P, predetermined force or pressure is applied to the pressure assembly 2 so that the pressure assembly is retreated in a predetermined distance. And, the force or the pressure applied to the pressure assembly 2, or the retreat distance of the pressure assembly 2 and so on is detected by the respective detection means 53, 53*a*, the pressure sensor 71*a*, the pressure gauge 72 or the contraction degree and so on. And, the detected force and so on may be displayed by the respective display means 57, 71, 80, 88 visually. Accordingly, the sitter may continue the shrink training of the perineum muscle P with interest and aim, watching the shrink and the relaxation degree of the perineum muscle P.

According to the invention, if the sitter shrinks the place which is pressed upwardly to be stimulated by the pressure head 20, the shrink training of the perineum muscle P is performed automatically so that he/she may easily do the shrink training for even the perineum region which has not been trained in ordinary times.

And, as the shrink and the relaxation degree of the perineum muscle P may be displayed visually, the sitter may continue the shrink training with goal and interest, watching the shrink and the relaxation degree of the perineum muscle P.

Further, the invention has an advantage that the sitter may sit on the pressure head 20 and may do the shrink training very conveniently and sanitarily because he/she may sit on the pressure head 20 without inserting a certain implement into the anus or the vagina.

The invention claimed is:

1. A perineum muscular power increase device comprising:
    a pressure assembly which presses the perineum muscle of a sitter upwardly and makes the center of the perineum region pressed upwardly;
    a first detection means which is provided at the pressure assembly and detects the force or the pressure that the pressure assembly is pushed downwardly by the shrink force of the perineum muscle while the user is shrinking the perineum muscle;
    a first display means which is connected to the first detection means and displays the force or the pressure applied to the pressure assembly visually;
    and wherein the shrink degree as well as the relaxation degree may be displayed visually through the first display part during the shrink training of the perineum muscle so that the sitter may watch the visually displayed degrees and may continuously do the shrink training with interest.

2. The perineum muscular power increase device of claim 1, wherein a controller is provided between the first display means and the first detection means.

3. The perineum muscular power increase device of claim 2, wherein a reset button is connected to the controller and the sitter may initialize the force data or the pressure data transmitted from the first detection means by the reset button.

4. The perineum muscular power increase device of claim 1, wherein the pressure assembly a comprises:
    a pressure head which presses the perineum muscle of the sitter upwardly;
    and a lifting means which is connected to the pressure head and moves it upwardly and downwardly.

5. The perineum muscular power increase device of claim 4, wherein the pressure head is connected to the lifting means at a hinge shaft and it may be rotated upwardly and downwardly, and an angle adjustment means is provided between the pressure head and the lifting means so that the front end or the base end of the pressure head may be ascended or descended, and the angle of the pressure head may be adjusted corresponding to the lifting means.

6. A muscular power increase device for perineum region comprising:
    a pressure assembly 2 which presses the perineum muscle P of a sitter upwardly and makes the center of the perineum region pressed upwardly;
    a fluid chamber 60 which is provided at the pressure assembly 2 and is pressed downwardly by the shrink force of the perineum muscle P as the sitter shrinks the perineum muscle P;
    and a second display part 71 which is connected to the fluid chamber 60 and displays the force or the pressure transmitted from the fluid chamber 60 visually.

7. The muscular power increase device for perineum region of claim 6, wherein the second display part 71 is a fluid pressure implement 72 which displays visually the pressure of the fluid transmitted from the fluid chamber 60 through an indication needle 72*a*.

8. The device for increasing perineum muscular power of claim 6, wherein a pressure sensor 71*a* and a controller 50 connected to the pressure sensor 71*a* are provided between the second display means 71 and the fluid chamber, and wherein the pressure sensor 71*a* detects the pressure of the fluid transmitted from the fluid chamber 60.

9. The device for increasing perineum muscular power of claim 8, wherein a reset button 56 is connected to the controller 50 and the sitter may initialize the pressure data transmitted from the pressure sensor 71*c* by the reset button 56.

10. The device for increasing perineum muscular power of claim 6, wherein the second display part 71 comprises:
    a cylinder 70 which is connected to the fluid chamber 60 and the piston 73 of which may be pushed by the pressure of the fluid transmitted from the fluid chamber 60;
    an elasticity means 75 which is provided in the cylinder 70 and pushes the piston 73 elastically toward the inflow direction of the fluid;
    and an indication needle 77 which is connected to the piston 73 and moves forwardly and backwardly to display the force or the pressure applied to the pressure assembly 2 visually.

11. A muscular power increase device for perineum region comprising:
    a pressure head 20 which presses the perineum muscle P of the sitter upwardly and makes the center of the perineum region pressed upwardly;
    an elasticity means 28 which pushes the pressure head 20 upwardly;
    a second detection means 53*a* which is provided under the pressure head 20 and detects the descending distance of the pressure head 20 or whether the pressure head 20 is contacted thereto by the shrink force of the perineum muscle P as the user shrinks the perineum muscle P;
    a third display part 80 which is connected to the second detection means 53A and displays the detected data visually.

12. The perineum muscular power increase device of claim 11, wherein a controller 50 is connected between the third display means 80 and the second detection means 53*a*.

13. A muscular power increase device for perineum region comprising:
    a pressure head 20 which presses the perineum muscle P of the sitter upwardly;
    an ascending and descending means 30 which is connected to the pressure head 20 and moves it upwardly and downwardly;
    an elasticity means 28 which pushes the ascending and descending means 30 upwardly;
    a second detection means 53*a* which is provided under the ascending and descending means 30 and detects the descending distance of it or whether the ascending and descending means 30 is contacted thereto by the shrink force of the perineum muscle P as the user shrinks the perineum muscle P;

a third display part 80 which is connected to the second detection means 53a and displays the detected data visually.

14. The perineum muscular power increase device of claim 11, wherein a controller 50 is connected between the third dispay means 80 and the second detection means 53a.

15. A muscular power increase device for perineum region comprising:

a pressure assembly 2 which presses the perineum region of the sitter upwardly and makes the center of the perineum muscle P pressed upwardly;

an elasticity means 28 which pushes the pressure assembly 2 upwardly;

a fourth display part 88 having an indication implement 85 which is connected to the pressure assembly 2 and is moved together with the pressure assembly 2 to display the descending distance of the pressure assembly 2 visually as the sitter shrinks the perineum muscle P.

* * * * *